United States Patent
Ortiz (10) Patent No.: US 7,534,247 B2
(45) Date of Patent: *May 19, 2009

(54) SHEATHLESS ANASTOMOTIC RING APPLIER DEVICE

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/121,216

(22) Filed: May 3, 2005

(65) Prior Publication Data

US 2006/0253137 A1 Nov. 9, 2006

(51) Int. Cl.
*A61B 17/10* (2006.01)
(52) U.S. Cl. .................................. 606/142; 606/153
(58) Field of Classification Search ................ 606/151, 606/153–157, 108, 139; 623/1.12
See application file for complete search history.

(56) References Cited

U.S. PATENT DOCUMENTS

| 5,855,312 | A | 1/1999 | Toledano |
| 6,117,159 | A * | 9/2000 | Huebsch et al. ............. 606/213 |
| 6,171,321 | B1 | 1/2001 | Gifford et al. |
| 6,428,550 | B1 | 8/2002 | Vargas et al. |
| 6,451,029 | B1 | 9/2002 | Yeatman |
| 6,485,496 | B1 | 11/2002 | Suyker et al. |
| 6,699,256 | B1 * | 3/2004 | Logan et al. ................. 606/153 |
| 6,830,575 | B2 * | 12/2004 | Stenzel et al. ............... 606/108 |
| 2003/0032967 | A1 | 2/2003 | Park et al. |
| 2003/0191482 | A1 | 10/2003 | Suyker et al. |

FOREIGN PATENT DOCUMENTS

EP 1520531 4/2005

OTHER PUBLICATIONS

European Search Report, dated Sep. 18, 2006, for EP Application No. 06252329.5.
Office Action dated Jan. 4, 2006, for U.S. Appl. No. 10/675,497, filed Sep. 30, 2003.

* cited by examiner

*Primary Examiner*—Todd E Manahan
*Assistant Examiner*—Jennifer L Hornberger
(74) *Attorney, Agent, or Firm*—Frost Brown Todd LLC (57) ABSTRACT

A surgical tool or applier for deploying an anastomotic ring comprises a handle connected to an elongate shaft that terminates in an anastomotic ring deployment mechanism. The ring deployment mechanism is moveable from an unactuated position to an actuated position. In order to prevent tissue from becoming trapped in the ring deployment mechanism during insertion or extraction of the tool, a plurality of panels are configured to enclose portions of the ring deployment mechanism during insertion and extraction, where the ring deployment mechanism is in the unactuated position. The panels are moveable with the ring deployment mechanism to the actuated position, in which the ring deployment mechanism is able to deploy the anastomotic ring.

15 Claims, 12 Drawing Sheets

SHEATHLESS ANASTOMOTIC RING APPLIER DEVICE

FIELD OF THE INVENTION

The present invention relates, in general, to surgery and, more particularly, to a device for performing a surgical procedure, such as on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

With some conventional anastomotic ring applier devices that use fingers or similar members to expand anastomotic rings, it may be possible for tissue to be trapped between the fingers of the applier device when it is inserted adjacent the proximate gastrointestinal tissue walls. Similarly, it may be possible for tissue to become trapped in the deployment mechanism during extraction of the device from the anastomosis site. The trapping of tissue between the fingers may result in undesirable consequences, such as pinching or tearing of the tissue, or even a compromise in the integrity of the anastomosis.

Some anastomotic ring applier devices known in the art incorporate a tubular sheath that is slideably located on the elongated shaft. The tubular sheath is typically in position over the ring deployment mechanism while the device is inserted adjacent the anastomosis site and during extraction of the device, and may be retracted to allow deployment of the ring. Such sheaths may cost time to retract and/or space for a retraction mechanism. Thus, it may be desirable to have an anastomotic ring applier device that provides a reduced likelihood of tissue becoming trapped in the ring deployment mechanism of the device, yet does not necessarily require a sheath for the fingers of the device.

BRIEF SUMMARY OF THE INVENTION

In one embodiment, an anastomotic ring applier device comprises a handle attached to an elongated shaft. The elongated shaft comprises an anastomotic ring deployment mechanism. The ring deployment mechanism comprises a plurality of panels adapted to cover portions of the ring deployment mechanism as it is inserted adjacent the anastomosis site and as it is extracted from the site, thereby preventing tissue from becoming trapped in the ring deployment mechanism.

In another embodiment, an anastomotic ring applier device comprises a handle attached to an elongated shaft comprising a proximal portion and a distal portion. The distal portion of the elongated shaft includes a ring deployment mechanism. The ring deployment mechanism comprises a plurality of fingers that are moveable from an unactuated position, in longitudinal alignment with the elongated shaft, to a second position, in which the fingers articulate outwardly from a longitudinal axis of the elongated shaft, in order to actuate a portion of the anastomotic ring. The device further comprises a plurality of panels that are adapted to cover the fingers of the ring deployment mechanism during insertion and extraction of the device. The panels are adapted to move with the fingers from the first position, in longitudinal alignment with the elongated shaft, to the second position, in which the fingers articulate outwardly from the shaft. Therefore, the device may prevent tissue from becoming caught between the fingers of the applier device during insertion and extraction.

In yet another embodiment, an anastomotic ring applier device may comprises a handle connected to a ring deployment mechanism by an elongated shaft. The ring deployment mechanism comprises a longitudinal end and a center portion. The device comprises an actuation mechanism that is adapted to move the longitudinal end of the ring deployment mechanism toward the center portion, thereby actuating a portion of the anastomotic ring. The applier device further comprises a plurality of panels that are adapted to cover portions of the longitudinal end of the ring deployment mechanism. The panels are adapted to move with the longitudinal end toward the center of the device. In this embodiment, the device may allow the surgeon to utilize a ring deployment mechanism to deploy an anastomotic ring, while guarding against the risk of tissue becoming trapped in the ring deployment mechanism during insertion and extraction of the instrument.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

DETAILED DESCRIPTION OF EMBODIMENTS OF THE INVENTION

Figure 1:
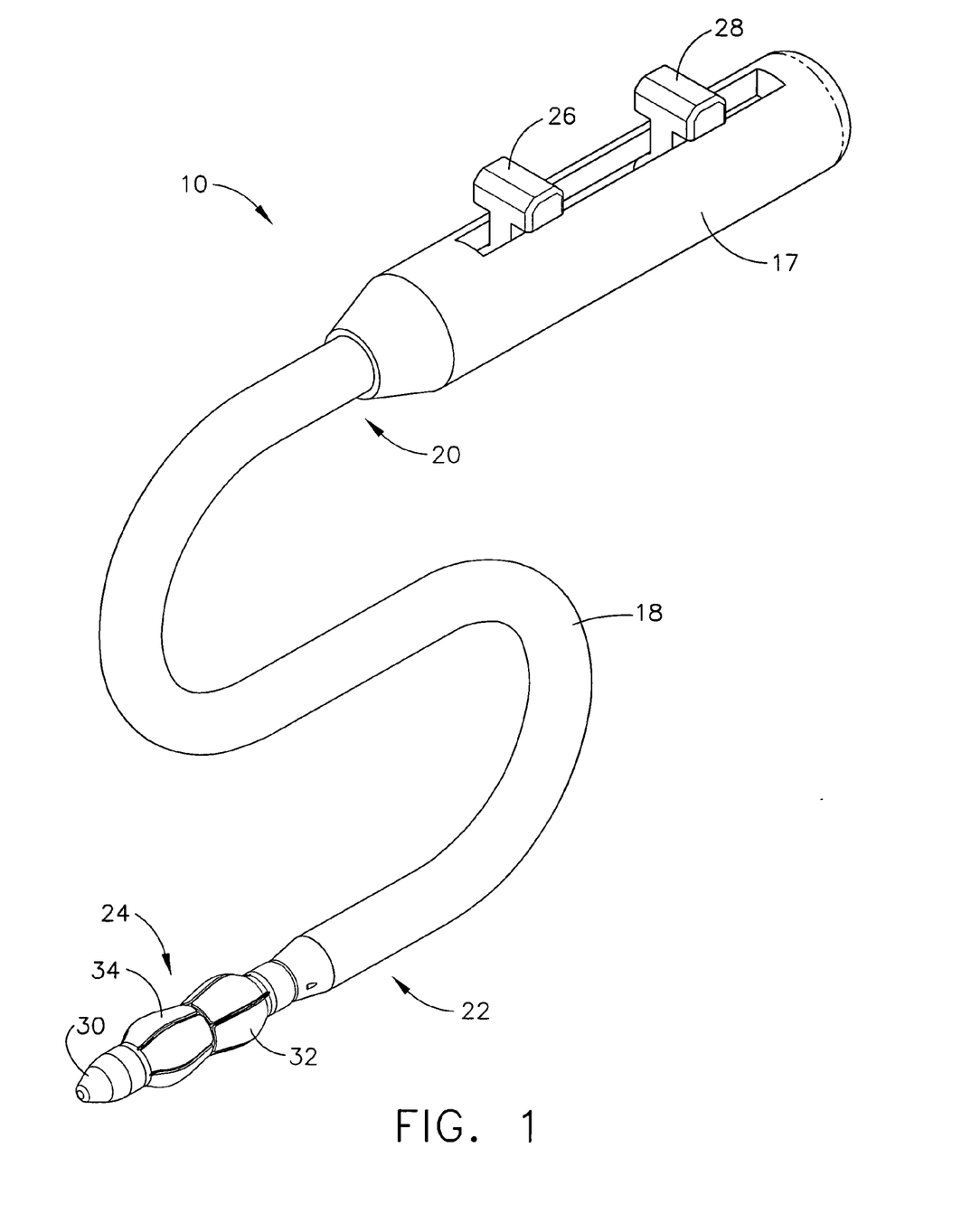
FIG. 1 is a perspective view of an anastomotic ring applier device.
Figure 2:
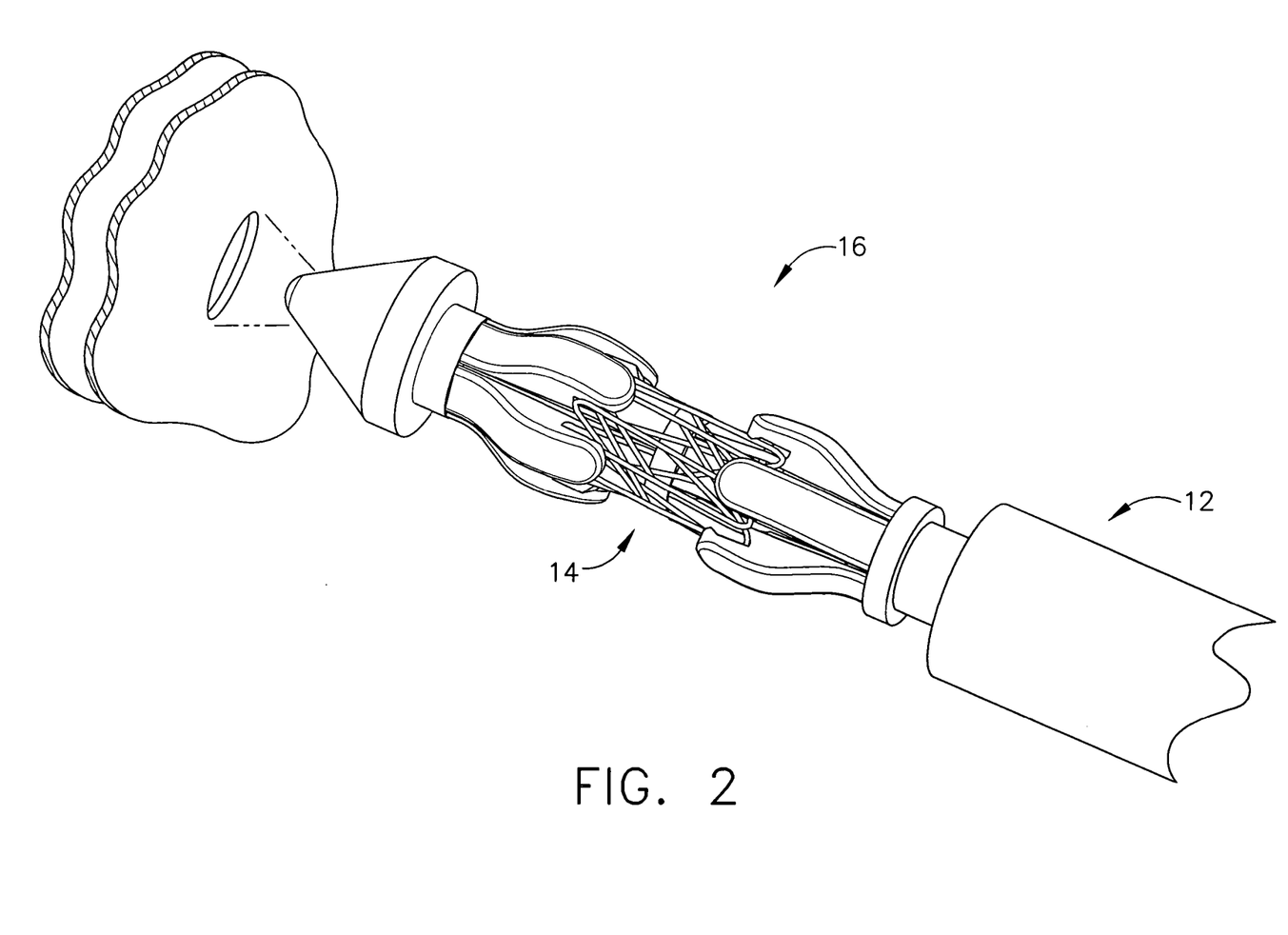
FIG. 2 is a partial perspective view of the distal portion of an anastomotic ring applier device holding an anastomotic ring in an unactuated position.
Figure 3:
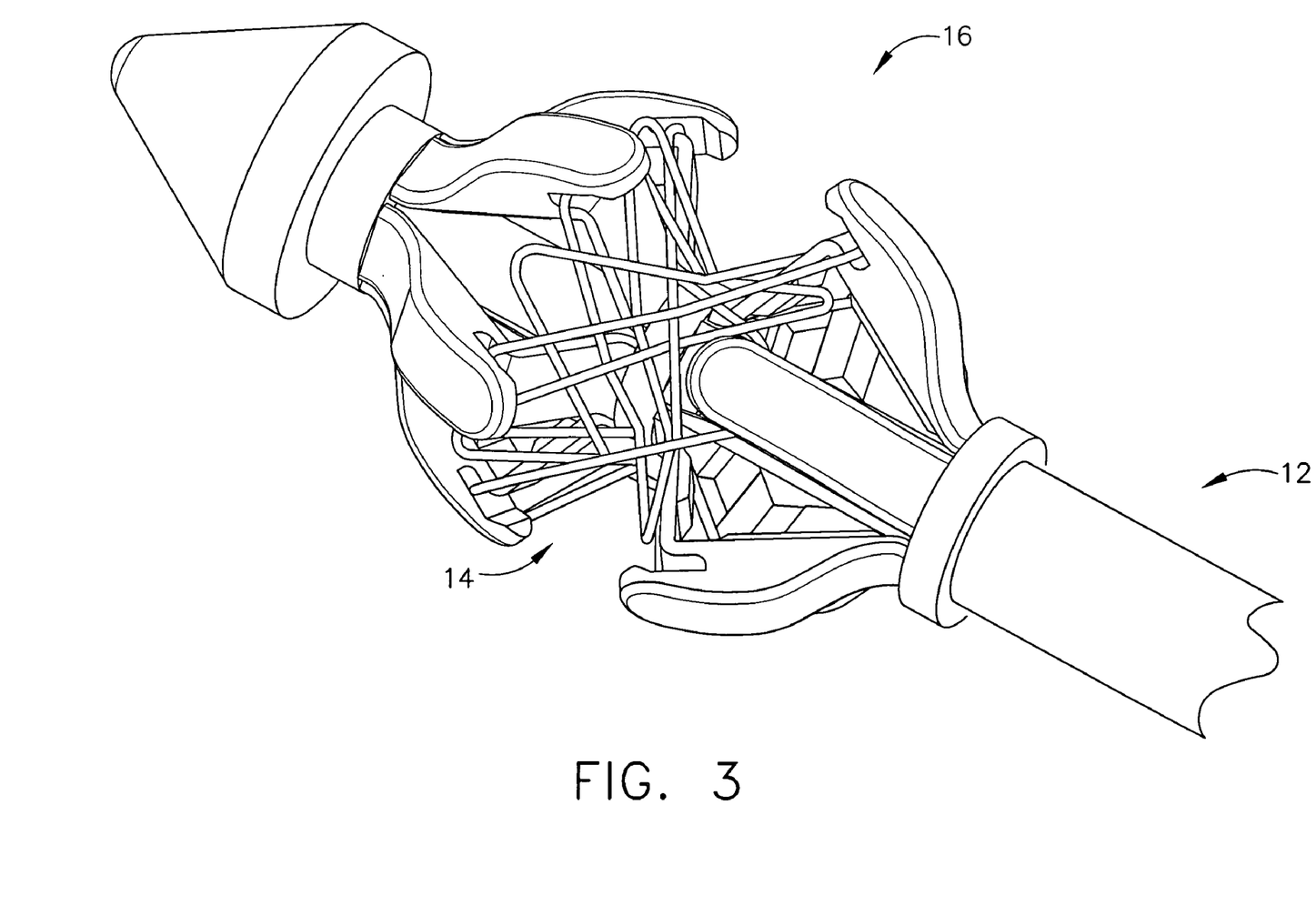
FIG. 3 is a partial perspective view of the distal portion of the device of FIG. 2 shown without panels, holding an anastomotic ring in the actuated position.
Figure 4:
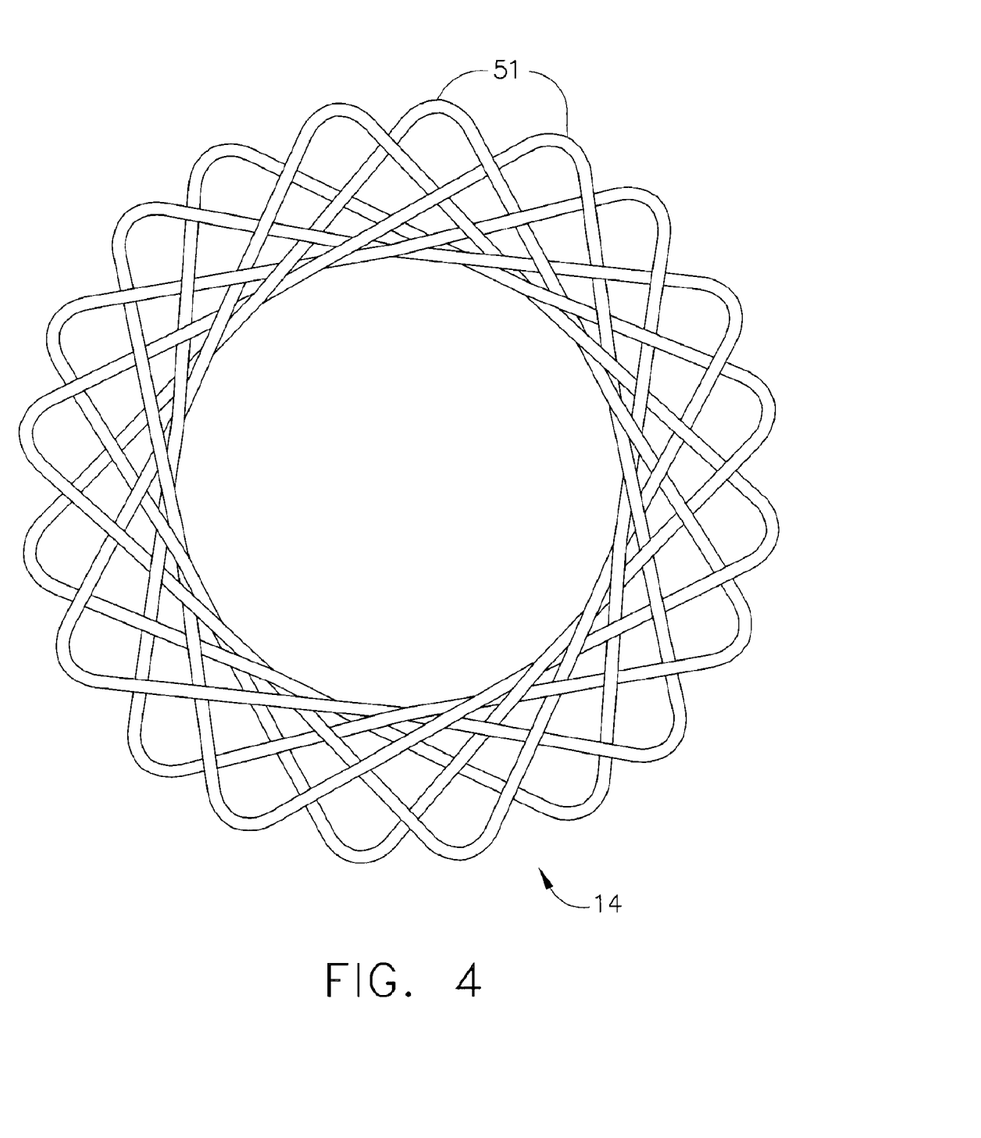
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Referring again to FIG. 1, applier 10 of the present example comprises a handle 17 connected to an elongated shaft 18 having a proximal end 20 and a distal end 22. As shown in FIG. 1, elongated shaft 18 is flexible. It will be appreciated that shaft 18 may be flexible either along its entire length or at one or more joints. Of course, shaft 18 may alternatively be rigid, resilient, malleable, or have other properties. Distal end 22 of shaft 18 comprises a ring deployment mechanism 24. Deployment mechanism 24 may be actuated by a button or lever located on handle 17. As shown in FIG. 1, handle 17 comprises a pair of actuator members 26, 28. In the present example, actuator members 26, 28 comprise sliders. The functioning of exemplary actuator members 26, 28 will be described below. It will be appreciated, however, that actuator members 26, 28 may take a variety of other forms and have a variety of other functions.

In the present example, ring deployment mechanism 24 is located proximal to a tip 30. Applier 10 includes a feature to prevent tissue from becoming trapped in deployment mechanism 24 when applier 10 is inserted or extracted from the anastomosis site. In FIG. 1, a plurality of proximal panels 32 and a plurality of distal panels 34 are pictured closed over ring deployment mechanism 24. In the closed position, proximal panels 32 are adjacent to one another with only minimal seams in between. Likewise, in the closed position, distal panels 34 are adjacent to one another with only minimal seams therebetween. Other suitable configurations for panels 32, 34 will be apparent to those of ordinary skill in the art.

Figure 5:
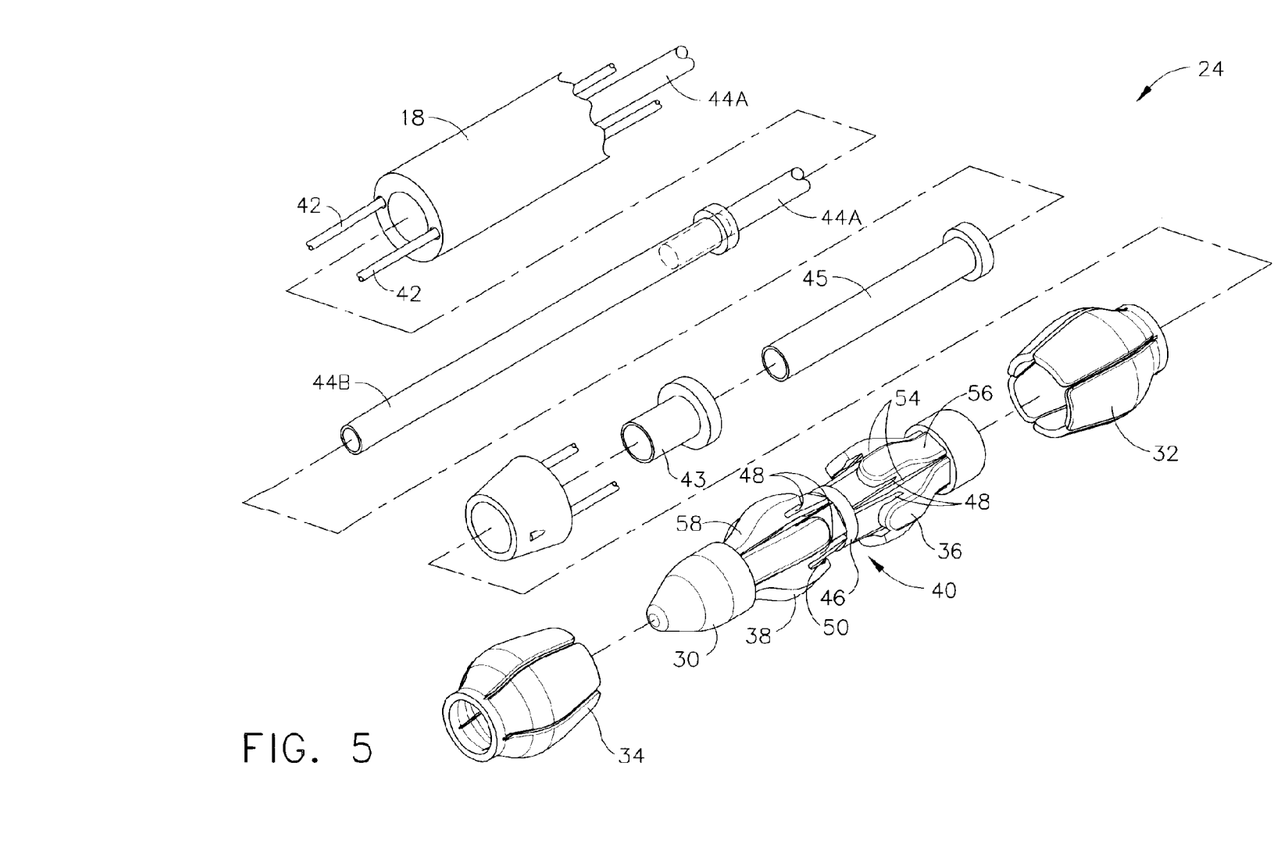
FIG. 5 is a perspective, exploded view of the anastomotic ring deployment mechanism of the device of FIG. 1.
Figure 12:
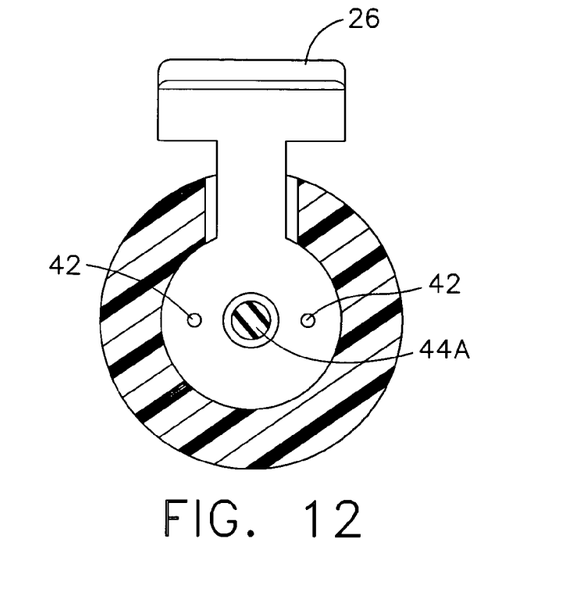
FIG. 12 is a cross-sectional view taken along Plane 12 of FIG. 11.
Figure 13:
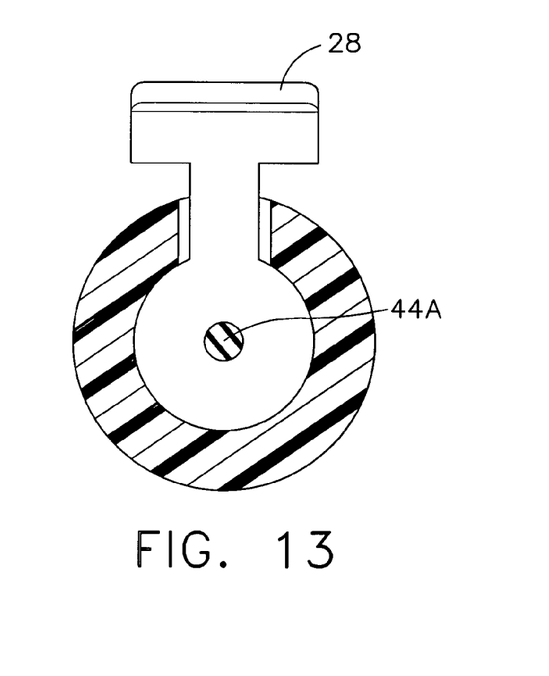
FIG. 13 is a cross-sectional view taken along Plane 13 of FIG. 11.

Referring to FIG. 5, ring deployment mechanism 24 is shown in an exploded view, demonstrating how proximal panels 32 fit over a plurality of proximal fingers 36, and distal panels 34 fit over a plurality of distal fingers 38. Ring deployment mechanism 24 comprises a stationary molded actuation member 40. Of course, molded actuation member 40 may be formed using any suitable method other than molding. In the present example, molded actuation member 40 comprises proximal fingers 36 and distal fingers 38. Molded actuation member 40 also has central portion 46, which is fixedly connected to middle tube 45. Middle tube 45 is fixed in distal end 22 of shaft 18. Proximal fingers 36 are connected to first actuator slider 26 via push/pull cables 42 of shaft 18 (FIG. 12). Push/pull cables 42 are in communication with an outer tube 43, which is fixedly connected with proximal fingers 36. Distal fingers 38 are connected to second actuator slider 28 via an inner tubes 44A, 44B of shaft 18 (FIG. 13). Inner tube 44A is fixedly connected with inner tube 44B. Proximal fingers 36 and distal fingers 38 are each in a double-hinged relationship with a central portion 46 of molded actuation member 40. Other suitable configurations for ring deployment mechanism 24 will be apparent to those of ordinary skill in the art.

Figure 8:
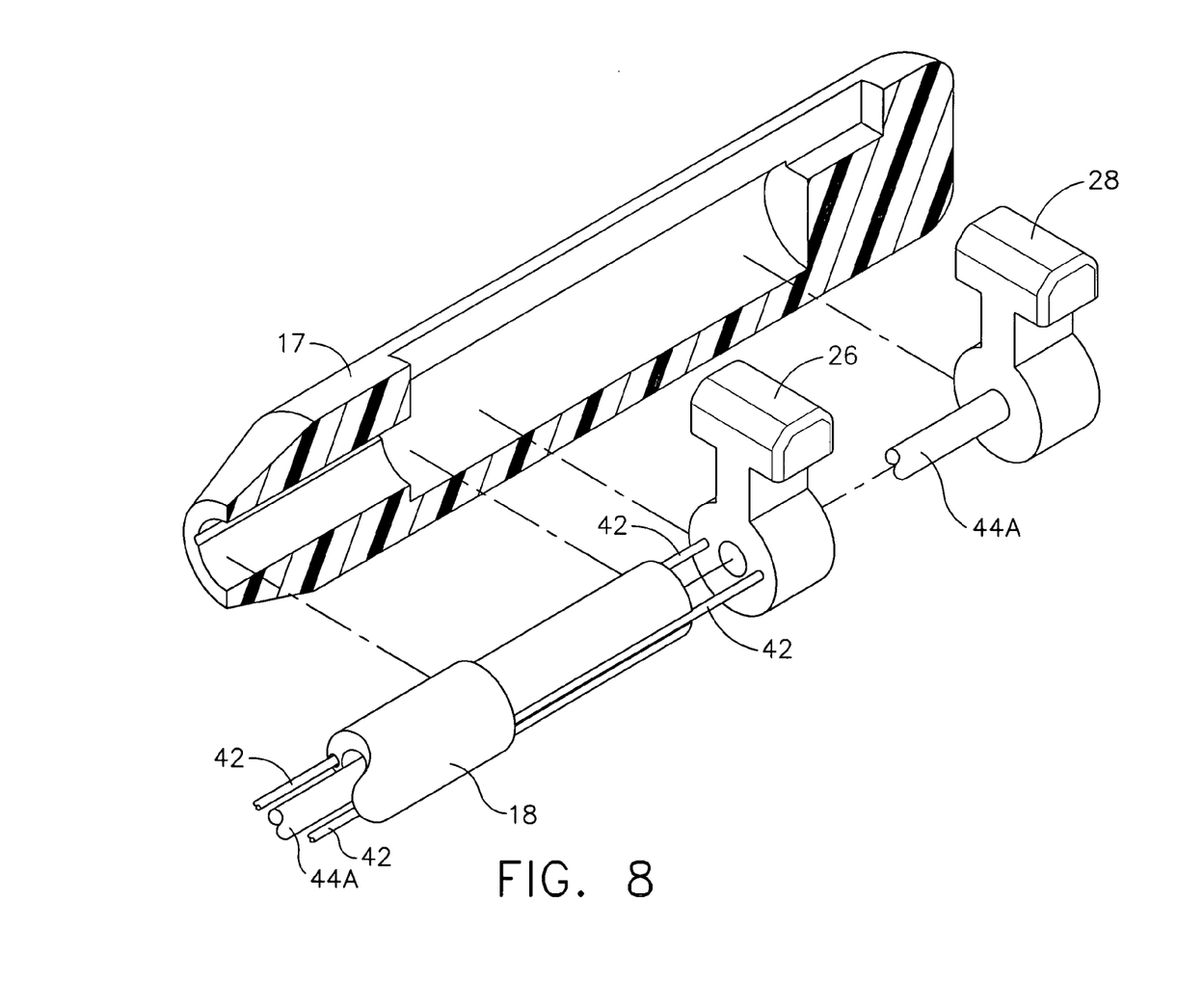
FIG. 8 is a perspective, cross-sectional exploded view of a proximal portion of the device of FIG. 1 with a left housing half omitted.
Figure 11:
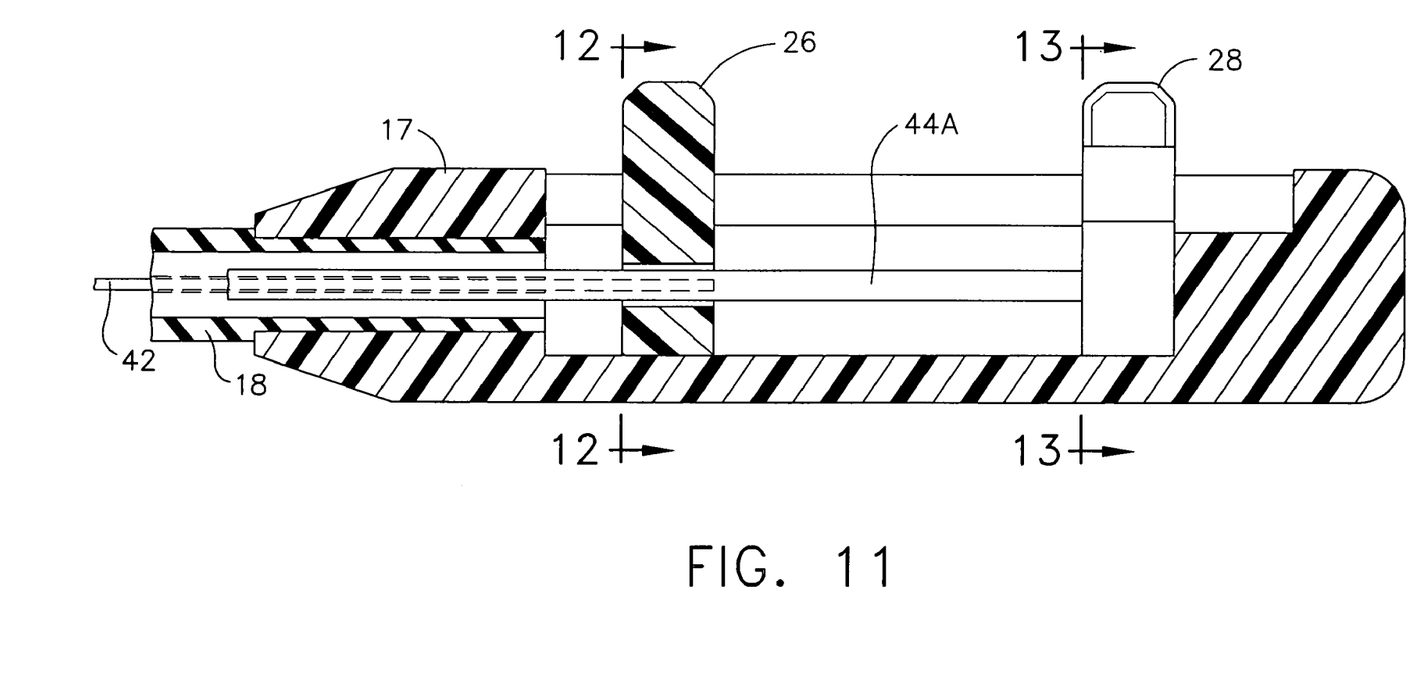
FIG. 11 is a partial cross-sectional view of a proximal portion of the device of FIG. 1.

FIGS. 8 and 11 show exemplary components of handle 17. In the present example, distal movement of first actuator slider 26 communicates distal motion to proximal fingers 36 via push/pull cables 42, thereby causing proximal fingers 36 to actuate outwardly in the manner of an umbrella due to their double-hinged relationship with central portion 46. Similarly, proximal movement of second actuator slider 28 communicates proximal motion to distal fingers 38 via inner tubes 44A, 44B, causing distal fingers 38 to actuate outwardly due to their double-hinged relationship with central portion 46. Thus, in this example, distal motion of first actuator slider 26 actuates a proximal portion of anastomotic ring 14 from the compressed position to the actuated position, while proximal motion of second actuator slider 28 actuates a distal portion of anastomotic ring 14 from the compressed position to the actuated position. It will be appreciated, however, that handle 17 may be configured such that first actuator slider 26 actuates distal fingers 38 and second actuator slider 28 actuates proximal fingers 36. Alternatively, any other suitable means, method, or mechanism for actuating an anastomotic ring from a compressed position to an actuated position may be used.

Proximal fingers 36 and distal fingers 38 of the present example comprise gripping slots 48, each of which include an inwardly-directed retention tip 50. Gripping slots 48 may assist in retaining anastomotic ring 14 when it is in the compressed position, as well as during intermediate steps of ring 14 deployment, while retention tip 50 may allow anastomotic ring 14 to disengage from petals 51 of anastomotic ring 14 after it has been deployed in the actuated position. Other suitable configurations for fingers 36, 38 will be apparent to those of ordinary skill in the art.

Figure 6:
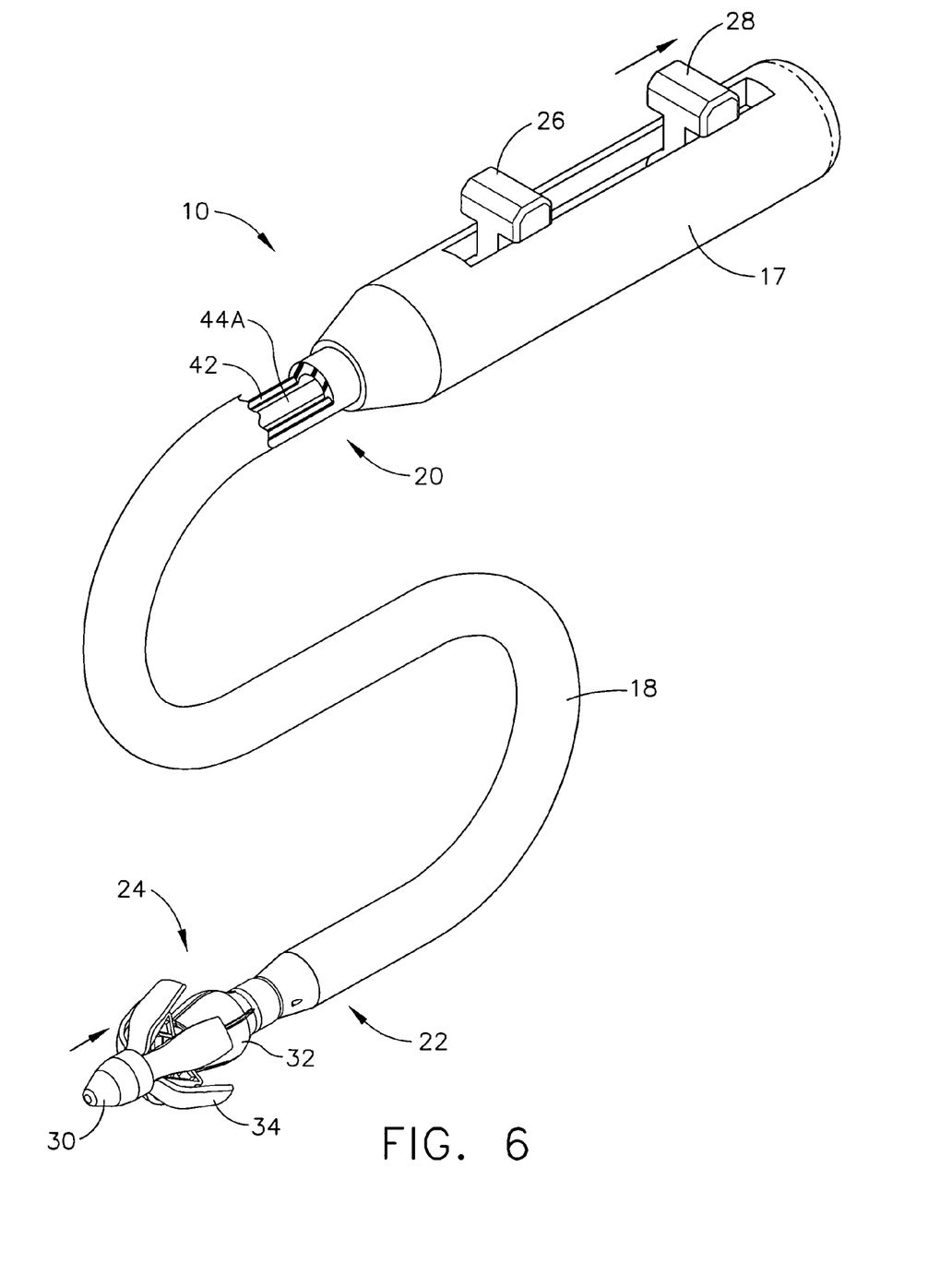
FIG. 6 is a perspective view of the anastomotic ring applier device of FIG. 1 with the distal portion of its ring deployment mechanism actuated.
Figure 7:
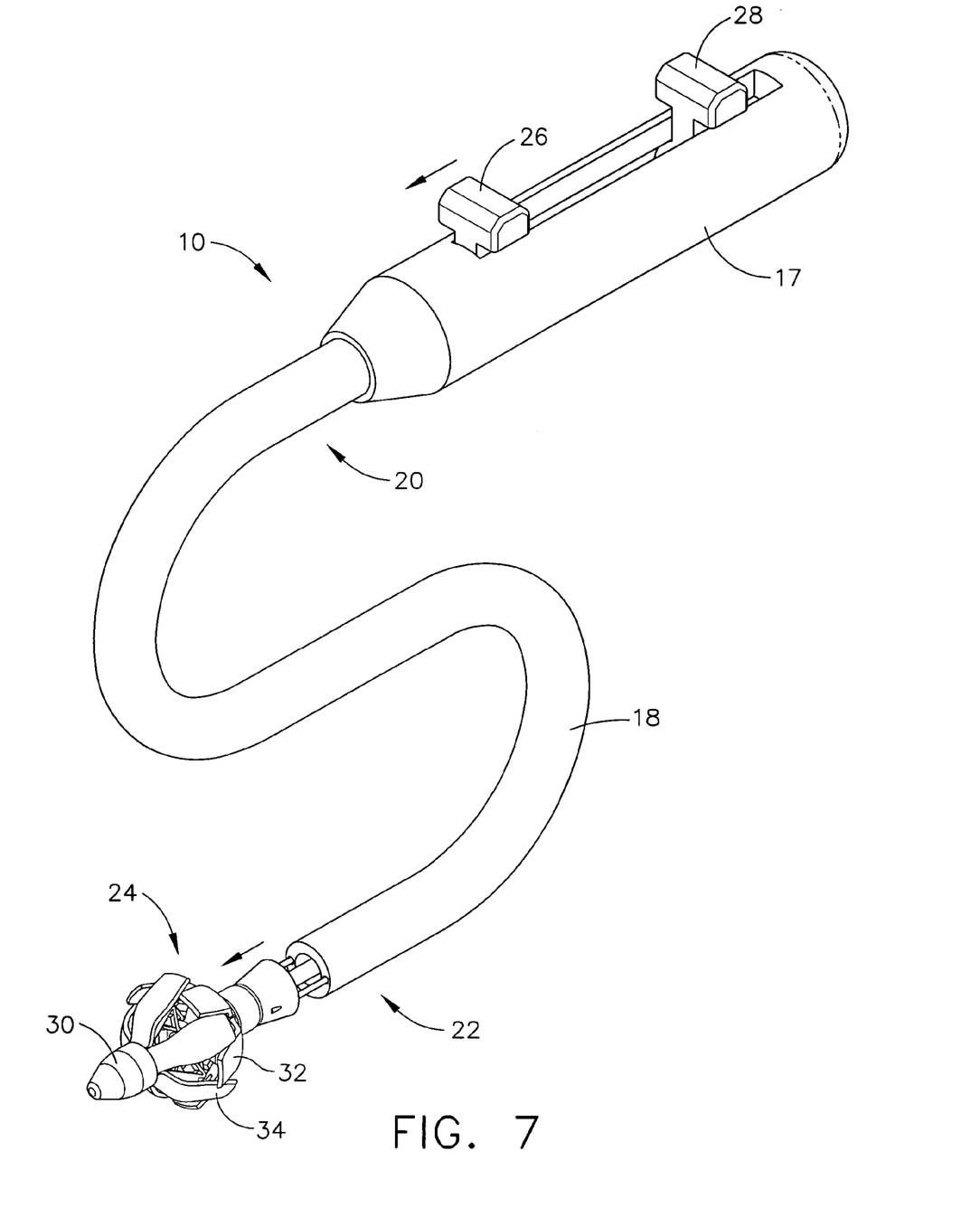
FIG. 7 is a perspective view of the device of FIG. 1 with both the distal portion and the proximal portion of its ring deployment mechanism actuated.

As best shown in FIG. 5, ring deployment mechanism 24 comprises gaps 54 between proximal fingers 36 and between distal fingers 38. Proximal panels 32 are adapted to cover proximal fingers 36, and distal panels 34 is adapted to cover distal fingers 38 when fingers 36, 38 are in the unactuated position in order to prevent tissue from becoming lodged in gaps 54 during insertion and extraction of applier 10. As shown in FIG. 6, proximal movement of second actuator slider 28 is adapted to cause distal fingers 38 to move to the actuated position, forcing distal panels 34 to separate and move with fingers 38 to the actuated position. In this manner, distal panels 34 may prevent tissue from becoming trapped in gaps 54 during insertion or extraction of applier 10 without interfering with deployment of anastomotic ring 14. Similarly, actuation of proximal fingers 36 causes proximal panels 32 to separate and move to the actuated position with fingers 36. FIG. 7 shows both proximal fingers 36 and distal fingers 38 in the expanded position, along with proximal and distal panels 32, 34, respectively, as a result of engagement of actuator sliders 26, 28.

In one embodiment, proximal panels 32 may be snapped onto a proximal end 56 of proximal fingers 36, while distal panels 34 may similarly be snapped onto a distal end 58 of distal fingers 38. However, it will be appreciated that panels 32, 34 may be fixed to or otherwise cooperate with fingers 36, 38 in a variety of alternative ways. By way of example only, proximal and distal panels 32, 34 may be secured to proximal and distal fingers 36, 38, respectively, by an adhesive, such as glue, by mechanical fasteners, or any other suitable means or method. While proximal panels 32 are shown as being integral with each other, it will be appreciated that proximal panels 32 may be configured in a variety of alternative ways. By way example only, each of the proximal panels 32 be physically separate from one another. In such an embodiment, for instance, each individual proximal panel 32 may be configured to fit on a corresponding individual proximal finger 36. Distal panels 34 and/or distal fingers 38 may likewise be subject to similar variations. Other suitable configurations for panels 32, 34, including but not limited to variations affecting their relationship with one another and/or their relationship with fingers 36, 38, will be apparent to those of ordinary skill in the art.

Panels 32, 34 may be comprised of the same material as fingers 32, 34, or any other suitable material. Other suitable materials for panels 32, 34 will be apparent to those of ordinary skill in the art.

Figure 9:
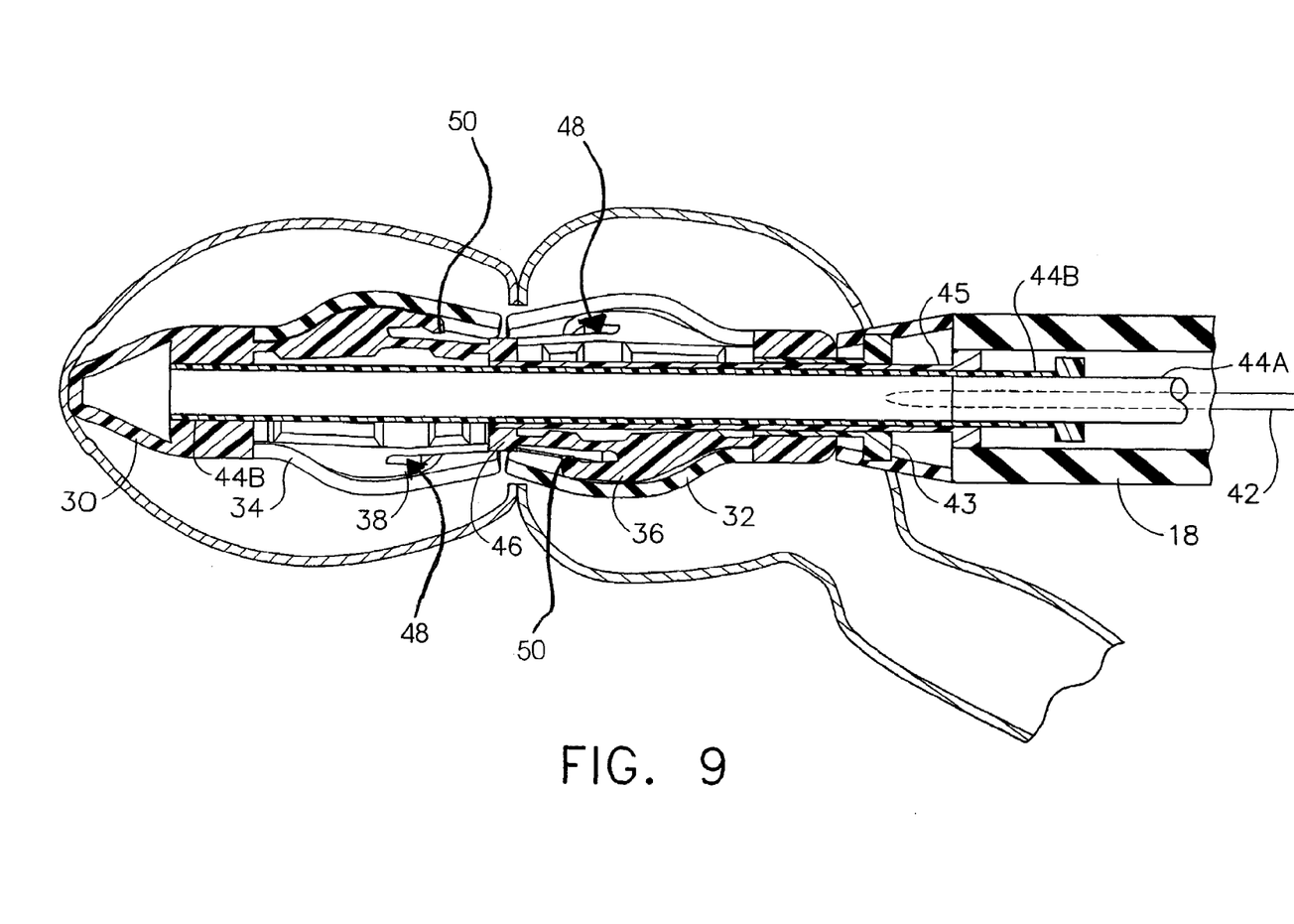
FIG. 9 is a partial cross-sectional view of the distal portion of the device of FIG. 1 inserted through an anastomotic opening.

In one example of operation, anastomotic ring 14 is held on ring deployment mechanism 24 by gripping slots 48 of proximal and distal fingers 36, 38. Applier 10 is inserted adjacent the anastomosis site, where an opening 60 is formed in two proximate gastrointestinal passages 62, 64, as shown in FIG. 9. As applier 10 is inserted, proximal and distal panels 32, 34 are in the closed or unactuated position, thereby preventing tissue from becoming trapped in gaps 54. Of course, panels 32, 34 may serve a variety of other purposes.

Figure 10:
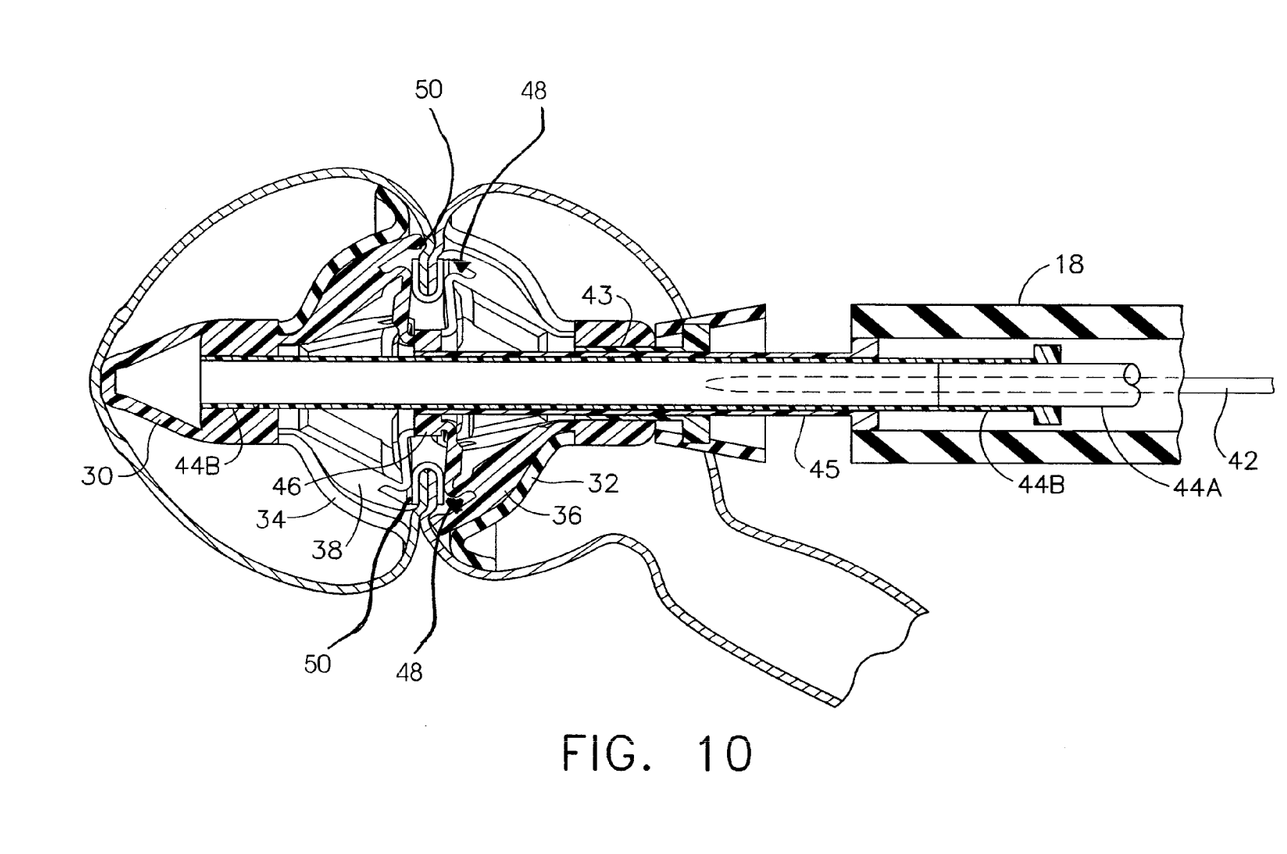
FIG. 10 is a partial cross-sectional view of the distal portion of the device of FIG. 1 forming an anastomotic attachment between proximate gastrointestinal tissue walls.

Referring now to FIG. 10, once ring deployment mechanism 24 is inserted into the anastomotic opening, first and second actuator sliders 26, 28 may be moved to their respective actuated positions. Because panels 32, 34 do not interfere with actuation of fingers 36, 38, actuation of sliders 26, 28 will cause fingers 36, 38 to actuate outwardly. This may expand anastomotic ring 14 from its compressed, cylindrically-shaped position to its actuated, hollow rivet-shaped position, forming an anastomotic attachment between the gastrointestinal tissue walls. When anastomotic ring 14 has been deployed, actuator sliders 26, 28 may be actuated to return fingers 36, 38 to an unactuated position. It will be appreciated that panels 32, 34 would return to the unactuated position with fingers 36, 38. With fingers 36, 38 and panels 32, 34 in the unactuated position, applier 10 may be withdrawn from the patient. During such withdrawal, panels 32, 34 may reduce the likelihood of tissue and the like from getting caught in fingers 36, 38. Other applications and methods of operating applier 10 will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument for implanting an anastomotic ring device, comprising:
   (i) a handle;
   (ii) a ring deployment mechanism configured to receive an anastomotic ring, the ring deployment mechanism having a plurality of distal fingers, a plurality of proximal fingers, and a central member positioned longitudinally between the plurality of distal fingers and the plurality of proximal fingers, wherein the ring deployment mechanism is adapted to move between an unactuated, generally cylindrical position and an actuated, hollow rivet-forming position, wherein each distal finger comprises a proximal segment and a distal segment, wherein the proximal segment of each distal finger is hingedly connected at a first end to a corresponding distal segment of each distal finger and hingedly connected at a second end to the central member, wherein the distal segment of each distal finger is hingedly connected at a first end to a corresponding proximal segment of each distal finger and hingedly connected at a second end to a distal portion of the ring deployment mechanism, wherein each proximal finger comprises a proximal segment and a distal segment, wherein the distal segment of each proximal finger is hingedly connected at a first end to a corresponding proximal segment of each proximal finger and hingedly connected at a second end to the central member, wherein the proximal segment of each proximal finger is hingedly connected at a first end to a corresponding distal segment of each proximal finger and hingedly connected at a second end to a proximal portion of the ring deployment mechanism;
   (iii) an elongate flexible shaft connecting the handle to the ring deployment mechanism;
   (iv) a first actuator operable to communicate a first actuating force to the plurality of distal fingers of the ring deployment mechanism and a second actuator operable to communicate a second actuating force to the plurality of proximal fingers of the ring deployment mechanism, wherein the first actuator and the second actuator are independently actuated; and
   (v) a plurality of distal panels adapted to cover the plurality of distal fingers of the ring deployment mechanism and a plurality of proximal panels adapted to cover the plurality of proximal fingers during insertion and extraction of the instrument, wherein the panels are adapted to move passively with the fingers from the unactuated position to the actuated position upon actuation of the first and second actuators.

2. The surgical instrument of claim 1, wherein the plurality of proximal fingers are independently moveable relative to the plurality of distal fingers of the ring deployment mechanism.

3. The surgical instrument of claim 2, wherein the plurality of proximal panels adapted to cover the plurality of proximal fingers of the ring deployment mechanism are independently moveable from the plurality of distal panels adapted to cover the plurality of distal fingers of the ring deployment mechanism.

4. The surgical instrument of claim 3, wherein the first actuator is operable to expand and retract the plurality of proximal fingers of the ring deployment mechanism and the second actuator is operable to expand and retract the plurality of distal fingers of the ring deployment mechanism.

5. The surgical instrument of claim 4, wherein actuation of the first actuator moves both the plurality of proximal fingers of the ring deployment mechanism and the plurality of proximal panels from the unactuated position to the actuated position.

6. The surgical instrument of claim 4, wherein actuation of the second actuator moves both the plurality of distal fingers of the ring deployment mechanism and the plurality of distal panels from the unactuated position to the actuated position.

7. The surgical instrument of claim 1, wherein the panels snap onto the ring deployment mechanism.

8. The surgical instrument of claim 1, wherein the panels comprise a first set of panels and a second set of panels, wherein the panels of the first set are integral with each other.

9. A surgical instrument for implanting an anastomotic ring device, comprising:
(i) a handle;
(ii) an elongate flexible shaft comprising a distal portion and a proximal portion connected to the handle;
(iii) a ring deployment mechanism configured to receive and deploy an anastomotic ring, the anastomotic ring comprising a first plurality of petals and a second plurality of petals, wherein the ring deployment mechanism comprises a plurality of distal fingers, a plurality of proximal fingers, and a central portion positioned longitudinally between the plurality of distal fingers and the plurality of proximal fingers, wherein each distal finger comprises a proximal segment and a distal segment, wherein the proximal segment of each distal finger is hingedly connected at a first end to a corresponding distal segment of each distal finger and hingedly connected at a second end to the central portion, wherein the distal segment of each distal finger is hingedly connected at a first end to a corresponding proximal segment of each distal finger and hingedly connected at a second end to a distal portion of the ring deployment mechanism, wherein the distal segment of each distal finger comprises an integral gripping slot, wherein each gripping slot of each distal finger is configured to receive a respective petal of the first plurality of petals of the anastomotic ring, wherein each proximal finger comprises a proximal segment and a distal segment, wherein the distal segment of each proximal finger is hingedly connected at a first end to a corresponding proximal segment of each proximal finger and hingedly connected at a second end to the central portion, wherein the proximal segment of each proximal finger is hingedly connected at a first end to a corresponding distal segment of each proximal finger and hingedly connected at a second end to a proximal portion of the ring deployment mechanism, wherein the proximal segment of each proximal finger comprises an integral gripping slot, wherein each gripping slot of each proximal finger is configured to receive a respective petal of the second plurality of petals of the anastomotic ring, wherein the central portion longitudinally separates the proximal segments of the distal fingers from the distal segments of the proximal fingers, wherein each of the plurality of fingers further comprises an inwardly directed retention tip adjacent to each gripping slot; and
(iv) a plurality of distal panels adapted to enclose at least a portion of the distal fingers of the ring deployment mechanism and a plurality of proximal panels adapted to enclose at least a portion of the proximal fingers of the ring deployment mechanism during insertion and extraction of the instrument, the distal panels and the proximal panels being passively moveable relative to the movement of the plurality of distal fingers and the plurality of proximal fingers, wherein the plurality of proximal fingers are actuated with a first actuator independently from the plurality of distal fingers actuated by a second actuator.

10. The surgical instrument of claim 9, further comprising gaps between pairs of the plurality of distal fingers and between the pairs of the plurality of proximal fingers.

11. The surgical instrument of claim 10, wherein the plurality of distal panels and the plurality of proximal panels are adapted to cover at least a portion of the gaps between the pairs of the plurality of distal fingers and the plurality of proximal fingers in the unactuated position.

12. The surgical instrument of claim 9, wherein the plurality of distal panels and the plurality of proximal panels are configured to be attached to at least a portion of the ring deployment mechanism.

13. The surgical instrument of claim 9, wherein the plurality of distal panels and the plurality of proximal panels each comprises a first plurality of panels and a second plurality of panels.

14. The surgical instrument of claim 13, wherein the first plurality of panels are integral with each other, and wherein the second plurality of panels are integral with each other.

15. A surgical instrument for implanting an anastomotic ring, comprising:
(i) a handle;
(ii) an elongate flexible shaft comprising a distal portion and a proximal portion, wherein the proximal portion is connected to the handle;
(iii) a ring deployment mechanism, the ring deployment mechanism being located on the distal portion of the elongate shaft and having a plurality of distal fingers and a plurality of proximal fingers, wherein the ring deployment mechanism is configured to receive a compressed anastomotic ring in the plurality of distal fingers and the plurality of proximal fingers, the anastomotic ring having a plurality of petals, the fingers being moveable from a first position longitudinally aligned with the elongate shaft to a second position in which the fingers actuate outwardly from a longitudinal axis of the elongate shaft to actuate at least a portion of an anastomotic ring, wherein each finger comprises a gripping slot, wherein each gripping slot of each finger is configured to receive a respective petal of the anastomotic ring, wherein each gripping slot is oriented substantially parallel with the longitudinal axis of the elongate shaft when the ring deployment mechanism is in an unactuated position, wherein the gripping slots open in a longitudinal direction substantially parallel to the axis of the elongate shaft when the ring deployment mechanism is in an unactuated position, wherein the number of gripping slots is equivalent to the number of fingers, wherein each of the plurality of fingers further comprises an inwardly directed retention tip adjacent to each gripping slot;

(iv) an actuation mechanism having a first actuator and a second actuator, the first actuator operable to move the plurality of distal fingers of the ring deployment mechanism and the second actuator operable to move the plurality of proximal fingers of the ring deployment mechanism independently from the first actuator; and (v) a plurality of distal panels adapted to enclose at least a portion of the plurality of distal fingers of the ring deployment mechanism and a plurality of proximal panels adapted to enclose at least a portion of the plurality of proximal fingers in a first position during insertion and extraction of the instrument, wherein the distal panels and the proximal panels are moveable to a second position, wherein the distal panels and the proximal panels are adapted to separate passively with the fingers to allow the ring deployment mechanism to actuate the first portion of the anastomotic ring.

* * * * *